(12) United States Patent
Lee et al.

(10) Patent No.: US 8,436,621 B2
(45) Date of Patent: May 7, 2013

(54) PH MEASUREMENT SYSTEM USING GLASS PH SENSOR

(75) Inventors: Jie Tae Lee, Daegu (KR); Dae Ryook Yang, Seoul (KR); Seung Jae Lee, Seongnam-si (KR); Su Whan Sung, Daegu (KR)

(73) Assignee: Kyungpook National University Industry-Academic Corporation Foundation (KR)

( * ) Notice: Subject to any disclaimer, the term of this patent is extended or adjusted under 35 U.S.C. 154(b) by 775 days.

(21) Appl. No.: 12/688,186

(22) Filed: Jan. 15, 2010

(65) Prior Publication Data

US 2010/0182022 A1  Jul. 22, 2010

(30) Foreign Application Priority Data

Jan. 16, 2009  (KR) .................. 10-2009-0003645
Sep. 23, 2009  (KR) .................. 10-2009-0090016

(51) Int. Cl.
*G01N 27/416* (2006.01)
(52) U.S. Cl.
USPC ........... 324/438; 204/433; 204/228.6; 436/51
(58) Field of Classification Search ............... 324/438
See application file for complete search history.

(56) References Cited

U.S. PATENT DOCUMENTS

| | | | | |
|---|---|---|---|---|
| 2,483,299 A | * | 9/1949 | Paully ........................ | 324/438 |
| 3,124,743 A | * | 3/1964 | Riseman .................... | 324/438 |
| 3,275,533 A | * | 9/1966 | Boronkay ................. | 205/788.5 |
| 3,405,048 A | * | 10/1968 | Soltz ......................... | 204/408 |
| 3,408,569 A | * | 10/1968 | Douglass et al. ......... | 324/123 R |
| 3,431,508 A | * | 3/1969 | Greer et al. ............... | 330/253 |
| 3,438,871 A | * | 4/1969 | Menichelli et al. ...... | 205/781.5 |
| 3,440,525 A | * | 4/1969 | Cardeiro ................... | 324/438 |
| 3,444,467 A | * | 5/1969 | Cliffgard .................. | 324/133 |
| 3,578,408 A | * | 5/1971 | Sirois et al. .............. | 422/75 |
| 3,662,256 A | * | 5/1972 | Eckfeldt .................... | 324/438 |
| 3,677,925 A | * | 7/1972 | Tamate et al. ............ | 204/406 |
| 3,786,345 A | * | 1/1974 | Mikkelsen ................ | 324/438 |
| 4,013,899 A | * | 3/1977 | Guicheteau ............... | 327/103 |
| 4,090,925 A | * | 5/1978 | Jungman ................... | 205/787.5 |
| 4,154,660 A | * | 5/1979 | Micko ....................... | 205/786.5 |
| 4,321,544 A | * | 3/1982 | Riseman ................... | 324/438 |
| 4,444,644 A | * | 4/1984 | Hiramoto et al. ........ | 204/406 |
| 4,447,309 A | * | 5/1984 | Morioka et al. ......... | 204/402 |
| 4,506,226 A | * | 3/1985 | Luce et al. ............... | 324/459 |
| 4,513,280 A | * | 4/1985 | Hannan et al. ........... | 205/778 |
| 4,767,994 A | * | 8/1988 | Hopkins et al. .......... | 324/438 |
| 4,777,444 A | * | 10/1988 | Beijk et al. ............... | 324/439 |
| 4,812,220 A | * | 3/1989 | Iida et al. ................. | 204/403.1 |

(Continued)

*Primary Examiner* — Patrick Assouad
*Assistant Examiner* — Lamarr Brown
(74) *Attorney, Agent, or Firm* — Daniel A. Thomson; Emerson Thomson Bennett, LLC

(57) ABSTRACT

A pH measurement system using a glass pH sensor includes a power supply applying a voltage to the glass pH sensor through a resistor; a detector detecting the output voltage of the glass pH sensor; and a calculator calculating the pH of a solution based on the detected output voltage. The resistor provides a resistance of at least ten times less than the equivalent internal resistance of the glass pH sensor. The pH measurement system can improve the response rate by reducing the time constant depending on the dynamic characteristics of the glass pH sensor, and it is possible to diagnose whether the pH measurement system is defective or not by calculating the equivalent internal resistance and the supply voltage of the glass pH sensor.

14 Claims, 6 Drawing Sheets

U.S. PATENT DOCUMENTS

| | | | | |
|---|---|---|---|---|
| 4,829,253 | A * | 5/1989 | Koluvek | 324/438 |
| 4,879,517 | A * | 11/1989 | Connery et al. | 324/438 |
| 4,912,417 | A * | 3/1990 | Gibboney et al. | 324/438 |
| 4,940,946 | A * | 7/1990 | Nazaryan | 324/438 |
| 4,961,163 | A * | 10/1990 | Bryan et al. | 702/116 |
| 4,963,815 | A * | 10/1990 | Hafeman | 205/777.5 |
| 4,998,068 | A * | 3/1991 | McKee, Jr. | 324/438 |
| 5,016,201 | A * | 5/1991 | Bryan et al. | 700/267 |
| 5,045,163 | A * | 9/1991 | Nyberg et al. | 205/792.5 |
| 5,046,028 | A * | 9/1991 | Bryan et al. | 702/116 |
| 5,124,659 | A * | 6/1992 | Frola et al. | 324/438 |
| 5,198,771 | A * | 3/1993 | Fidler et al. | 324/438 |
| 5,218,304 | A * | 6/1993 | Kinlen et al. | 324/438 |
| 5,268,852 | A * | 12/1993 | Forsythe et al. | 702/58 |
| 6,098,463 | A * | 8/2000 | Goldberg | 73/646 |
| 6,353,323 | B1 * | 3/2002 | Fuggle | 324/438 |
| 6,392,416 | B1 * | 5/2002 | Keech | 324/438 |
| 6,624,637 | B1 * | 9/2003 | Pechstein | 324/438 |
| 6,650,119 | B2 * | 11/2003 | Nonaka et al. | 324/425 |
| 6,894,502 | B2 * | 5/2005 | Feng et al. | 324/438 |
| 7,038,459 | B2 * | 5/2006 | Wakabayashi | 324/438 |
| 7,511,504 | B2 * | 3/2009 | Pechstein et al. | 324/438 |
| 7,638,157 | B2 * | 12/2009 | Hsiung et al. | 427/2.11 |
| 7,924,017 | B2 * | 4/2011 | Ammann et al. | 324/438 |
| 8,016,991 | B2 * | 9/2011 | Scheying et al. | 204/433 |
| 2002/0027085 | A1 * | 3/2002 | Stori et al. | 205/775 |
| 2003/0132755 | A1 * | 7/2003 | Feng et al. | 324/438 |
| 2003/0178305 | A1 * | 9/2003 | Catalano et al. | 204/433 |
| 2004/0238360 | A1 * | 12/2004 | Scheying et al. | 204/433 |
| 2006/0060475 | A1 * | 3/2006 | Applegate et al. | 205/775 |
| 2009/0211924 | A1 * | 8/2009 | West et al. | 205/787.5 |
| 2011/0140703 | A1 * | 6/2011 | Chiao et al. | 324/438 |

* cited by examiner

PH MEASUREMENT SYSTEM USING GLASS PH SENSOR

CROSS REFERENCE TO RELATED APPLICATION

The present application claims priority to Korean Patent Application Numbers 10-2009-0003645 filed on Jan. 16, 2009 and 10-2009-0090016 filed on Sep. 23, 2009, the entire contents of which applications are incorporated herein for all purposes by this reference.

BACKGROUND

The present invention relates to a system for measuring the pH of a solution using a glass pH sensor, in particular, to one which can improve the response rate by reducing the time constant of the glass pH sensor using an external supply voltage applied through a resistor and diagnose a defect by calculating the characteristics of the glass pH sensor.

In addition, the present invention relates to a pH measurement system using a glass pH sensor, in particular, to one which can reduce the pH measurement time of a solution using a feedback circuit.

DESCRIPTION OF RELATED ART

In general, measurement of the hydrogen ion concentration (pH) of a solution is very important in terms of chemical, biological, and physical treatment.

Semiconductor sensors and optical sensors are under development for use as pH measurement sensors. Many theoretical research projects and their applications about pH sensors have been carried out since the pH response of oxide glasses was first reported. Since the pH sensor is mechanically and chemically stable, it is very important in terms of application and can be used in a wide range of solvents.

The glass pH sensor is relatively fast and is effectively applicable to on-line measurement. However, more rapid response characteristics are required in some applications such as identification tanks, end-point estimation, auto-titrators, etc.

The dynamic response of the glass pH sensor is generally composed of a rapid response to the quasi-equilibrium and a slow drift resulting from ion infiltration through a glass membrane.

The response to the quasi-equilibrium state can be explained using an equilibrium circuit, as shown in FIG. 1, which has a very high internal resistance and capacitance. In this case, FIG. 1 FIG. 1A shows a symbol of a typical glass pH sensor, and FIG. 1B shows an equivalent circuit of the glass pH sensor shown in FIG. 1A.

As shown in FIG. 1A, a typical glass pH sensor 10 has one body, composed of a thin glass bulb, sensitive to the pH of a solution, and a reference electrode. The pH-sensitive glass membrane has an internal resistance of about $10^8 \Omega$ and a capacitance of about $10^2$ pF.

Since the equivalent internal capacitance results from the electrical double layers of the electrode and the solution and is distributed across the body of the glass pH sensor 10, the glass pH sensor 10 can be simplified into the equivalent circuit, shown in FIG. 1B, which is effective for low-frequency operation.

The capacitance of the equivalent internal capacitor 16 is relatively uniform, whereas the resistance of the equivalent internal resistor 12 is very sensitive to and varies according to temperature.

An ideal variation in an output voltage of the glass pH sensor 10 is 59.16 mV per unit change in pH at 25° C.

The measurement system using the glass pH sensor 10 measures the output voltage of the glass pH sensor 10 using a calculation amplifier that has an input resistance of $10^{12} \Omega$ or more and a very low input bias current.

FIG. 2 is a diagram schematically illustrating a pH measurement system using a conventional glass pH sensor.

Referring to FIG. 2, the pH of a solution can be calculated by detecting an output voltage of the glass pH sensor 10 using a calculation amplifier 20.

The dynamic response of the glass pH sensor 10 results from the charging time of the equivalent internal capacitor 16 through the equivalent resistor 12 of the glass membrane, and corresponds to a time constant. In this case, dynamic characteristics are expressed by Formula 1 below.

$$E_b(s) = \frac{1}{\tau s + 1} E(s) \quad \text{Formula 1}$$
$$\tau = RC$$

In Formula 1 above, R is a resistance of the equivalent internal resistor 12 of the glass pH sensor 10, and C is a capacitance of the equivalent internal capacitor 16 of the glass pH sensor 10.

However, the conventional measurement system may not be applicable in practice since it requires a time of 5 seconds or more, which is excessively long in some applications, to reach a steady-state pH value.

In this measurement system, the capacitance C of the equivalent internal capacitor 16 can be reduced by performing positive feedback on an amplified sensor output through a capacitor having a small value. At this time, dynamic characteristics are expressed by Formula 2 below.

$$E_b(s) = \frac{1}{\tau s + 1} E(s) \quad \text{Formula 2}$$
$$\tau = R(C - \alpha C_1)$$

In Formula 2 above, $\alpha$ is an amount of positive feedback that can be adjusted by a variable resistor.

In this case, as can be seen from Formula 2 above, the time constant of the glass pH sensor 10 decreases due to a feedback capacitor C1.

However, the measurement system may be unstable when $C - \alpha C_1$ is negative due to a variation in the capacitance C of the equivalent internal capacitor 16. In addition, it is impractical to set $C - \alpha C_1$ to a very small value. Accordingly, it is difficult to stably maintain the time constant of the glass pH sensor 10 under such conditions that the internal resistance R of the glass pH sensor 10 varies significantly.

In addition, the measurement system becomes unstable due to an increase in the amplitude of the feedback since it is based on the positive feedback. Furthermore, it is difficult to ensure the size and stability of the feedback and to find a determined time constant.

In order to diagnose whether the glass pH sensor 10 is defective or not, a method of applying a square wave voltage or current to the glass pH sensor 10 is also proposed.

Both the equivalent internal resistance R and the equivalent voltage E of the glass pH sensor 10 can be measured by applying a series of small current pulses (10 nA or less) to the glass pH sensor 10. The internal resistance R measured in this manner is used in diagnosing whether the glass pH sensor 10 is defective or not.

However, the foregoing measurement method has a problem in that the response of the glass pH sensor 10 is not rapid since this method cannot reduce the time constant of the glass pH sensor 10 by the equivalent internal resistor 10 and the equivalent capacitor 16.

Furthermore, the conventional measurement system may not be applicable in practice since it requires a time of 5 seconds or more, which is excessively long in some applications, to reach a steady-state pH value.

The information disclosed in this Background of the Invention section is only for enhancement of understanding of the background of the invention and should not be taken as an acknowledgment or any form of suggestion that this information forms the prior art that is already known to a person skilled in the art.

BRIEF SUMMARY

Various embodiments provide a pH measurement system having a glass pH sensor, which can reduce the time constant of the measurement system and calculate an internal resistance and a supply voltage corresponding to an equivalent circuit of the glass pH sensor.

There is also provided a pH measurement system having a glass pH sensor, which can reduce measurement time when measuring the pH of a solution.

In at least one embodiment, the pH measurement system using a glass pH sensor may include a power supply applying a voltage to the glass pH sensor through a resistor; a detector detecting the output voltage of the glass pH sensor; and a calculator calculating the pH of a solution based on the detected output voltage. The resistor may provide a resistance of at least ten times less than the equivalent internal resistance of the glass pH sensor.

The detector may include a power supply applying a voltage to the glass pH sensor a calculation amplifier and a feedback capacitor.

The glass pH sensor may have a time constant expressed by $R_1(C-\alpha C_1)/(1+\beta)$, where $R_1$ is the resistance of the resistor, $C_1$ is the capacitance of the glass pH sensor, R is the equivalent internal resistance of the glass pH sensor, C is the equivalent internal capacitance of the glass pH sensor, $\alpha$ is the gain of the calculation amplifier, and $\beta$ is $R_1/R$.

The power supply may provide a square wave, and the calculator may produce $\beta$ based on the output voltage of the glass pH sensor with respect to two different voltages of the square wave.

The square wave may have a pulse width greater than the time constant.

The output voltage of the glass pH sensor may be a normalized voltage.

The calculator may produce the equivalent internal voltage of the glass pH sensor based on the output voltage of the pH glass sensor with respect to the two different voltages of the square wave.

The calculator may produce the equivalent internal resistance of the glass pH sensor based on $\beta$ in order to enable diagnosis on whether the glass pH sensor is defective or not.

The glass pH sensor may be implemented with an equivalent circuit. The equivalent circuit may include one equivalent power source; two or more equivalent resistors connected in series to the equivalent power source; a first equivalent capacitor connected in parallel to the first equivalent resistor; and a second equivalent capacitor connected in series to the second equivalent resistor.

The pH measurement system may further include a feedback circuit provided between the glass pH sensor and the calculator. The feedback circuit may receive the output voltage of the glass pH sensor from the detector, generate a feedback voltage by adjusting the output voltage through a variable resistor, and reapply the feedback voltage to the glass pH sensor.

The feedback circuit may be implemented with an embedded Central Processing Unit (CPU).

The dynamic characteristics of the glass sensor may be expressed by the following Formula.

$$G_{GLASS}(s)=(b_1s+1)/(a_2s^2+a_1s+1)$$

A transition function between the output voltage detected by the detector and the feedback voltage to be inputted again into the detector may be expressed by the following Formula.

$$U(s)=(k_gs+k_1)Y(s)/\tau_Fs+1$$

In the above Formula, $Y(s)$ is the output voltage of the glass pH sensor, $U(s)$ is the feedback voltage, $t_F$ is the time constant of the glass pH sensor, $k_1$ and $k_2$ are variables that vary according to a variable resistance.

The embedded CPU may adjust the feedback voltage based on a result, obtained by calculating the following Formulas.

$$z_k=e^{-h/\tau F}z_{k-1}+(1-e^{-h/\tau F})y_k$$

$$u_k=(k_2/\tau_F)y_k+(k_1-(k_2/\tau_F))z_k$$

In the above Formulas, h is sampling time, and the subscript k indicates $k^{th}$ sampling.

According to exemplary embodiments of the present invention as set forth above, the pH measurement system using a glass pH sensor can improve the response rate by reducing the time constant depending on the dynamic characteristics of the glass pH sensor by the application an external power source and a feedback capacitor through a resistor.

The pH measurement system using a glass pH sensor has an effect capable of diagnosing whether the glass pH sensor is defective or not by calculating the equivalent internal resistance and the supply voltage of the glass pH sensor by measuring the normalized output voltage of the pH sensor with respect to different voltages of a square wave, supplied as an external supply voltage.

In addition, the pH measurement system using a glass pH sensor can reduce the measurement response time of the glass pH sensor by feeding back the detected output voltage through the feedback circuit to the detector, which detects the output voltage of the glass pH sensor, and thus rapidly measure the pH.

Furthermore, since the feedback circuit of the pH measurement system using a glass pH sensor is implemented with the embedded CPU system, it is possible to diagnose whether the pH measurement system is defective or not so that the follow-up measures can be properly performed.

The methods and apparatuses described herein have other features and advantages which will be apparent from or are set forth in more detail in the accompanying drawings, which are incorporated herein, and the following Detailed Description, which together serve to explain certain principles of the several embodiments.

BRIEF DESCRIPTION OF THE DRAWINGS

The method and apparatus may take physical form in certain parts and arrangement of parts, at least one embodiment of which will be described in detail in this specification and illustrated in the accompanying drawings which form a part hereof and wherein.

DETAILED DESCRIPTION

Reference will now be made in detail to various embodiments, examples of which are illustrated in the accompanying drawings and described below. It will be understood that the present description is not intended to limit the invention(s) to the exemplary embodiments. On the contrary, the invention(s) is/are intended to cover not only the exemplary embodiments, but also various alternatives, modifications, equivalents, and other embodiments, which may be included within the spirit and scope of the invention as defined by the appended claims At least one embodiment applies positive feedback through a capacitor in order to reduce variation in the equivalent internal capacitance of a glass pH sensor and adds an external voltage, applied through a resistor, in order to reduce variation in the equivalent internal resistance. The external voltage can be used to charge the equivalent internal capacitor of the glass pH sensor, thereby reducing a time constant.

Figure 1A:
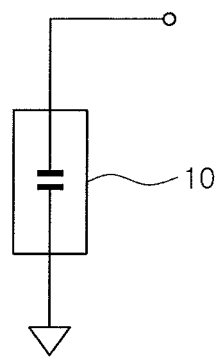
FIG. 1A is a diagram illustrating a symbol of a typical glass pH sensor.
Figure 1B:
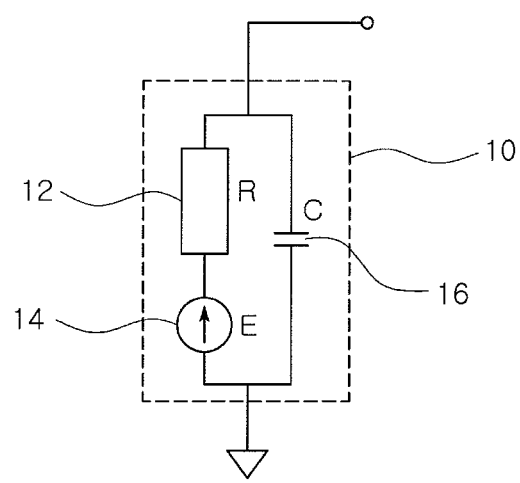
FIG. 1B is a diagram illustrating an equivalent circuit of the glass pH sensor shown in FIG. 1A.
Figure 2:
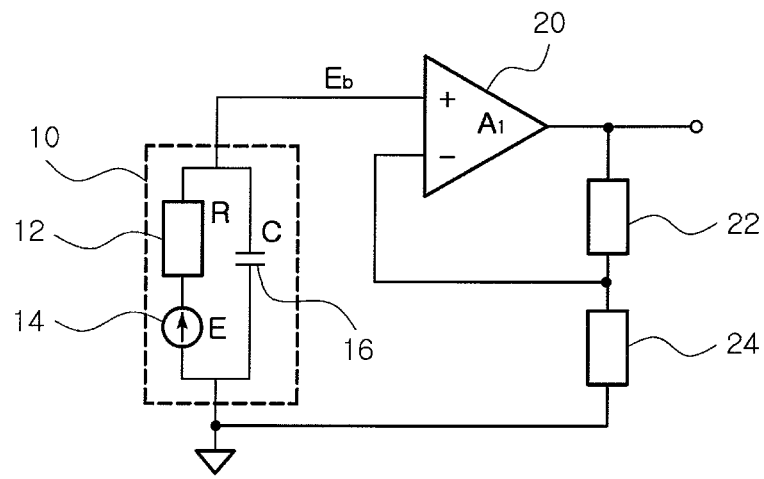
FIG. 2 is a diagram schematically illustrating a pH measurement system using a conventional glass pH sensor.
Figure 3:
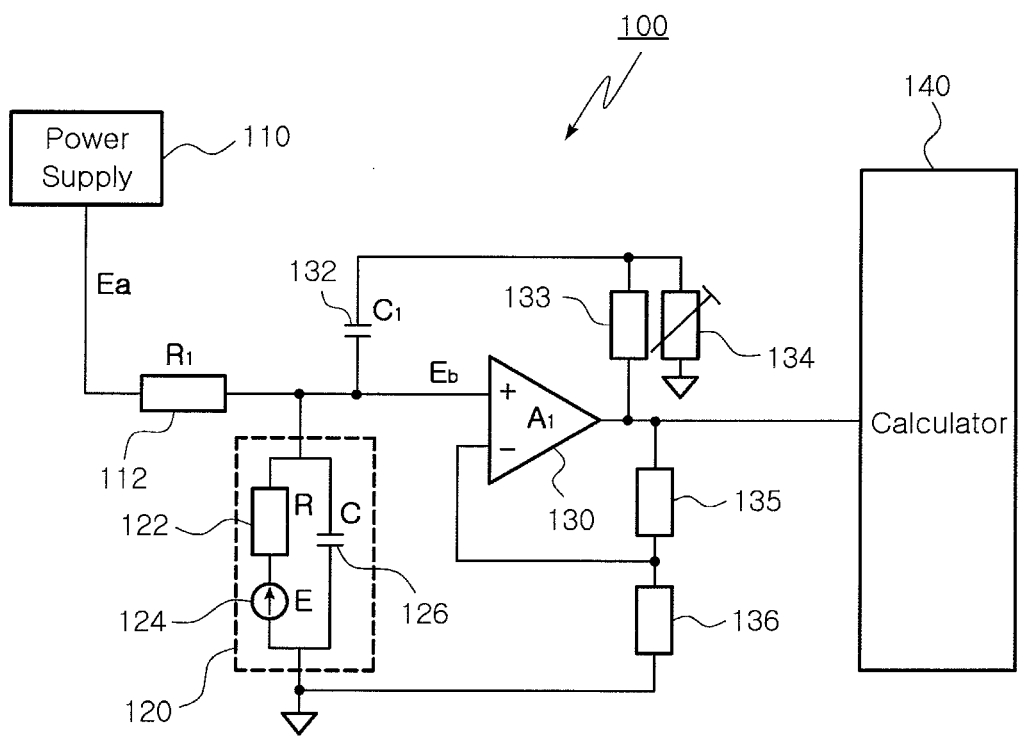
FIG. 3 is a diagram schematically illustrating a measurement system using a glass pH sensor in accordance with a first exemplary embodiment of the invention.

FIG. 3 is a diagram schematically illustrating a measurement system using a glass pH sensor in accordance with an exemplary embodiment of the invention.

The measurement system 100 using a glass pH sensor includes a power supply 110 applying power through a resistor 112, a glass pH sensor 120 immersed into a solution to be measured, a detector 130 through 136 detecting the output voltage of the glass pH sensor 120, and a calculator 140 calculating the pH value of the solution to be measured based on the detected output voltage of the glass pH sensor 120.

The power supply 110 is a power supply device providing a constant voltage Ea, and applies the voltage Ea to the glass pH sensor 120 through the resistor 112.

The resistor 112 has a resistance smaller than the resistance R of an equivalent internal resistor 122 of the glass pH sensor. In one embodiment, the resistor 112 can have a resistance ten times less than the resistance R.

As shown in FIG. 3, the glass pH sensor 120 includes electrical components such as the equivalent internal resistor 122, an equivalent internal power source 124, and an equivalent internal capacitor 126.

The detector 130 through 136 is an integrator, which includes a calculation amplifier 130, a feedback capacitor 132, a feedback resistor 133, a variable resistor 134, a first gain resistor 135, and a second gain resistor 136. The calculation amplifier 130 has a high input resistance and a low bias input current, the feedback capacitor 132 and the feedback resistor 133 feed back the output of the calculation amplifier 130, and the variable resistor 134, the first gain resistor 135, and the second gain resistor 136 adjust the gain of the calculation amplifier 130.

The calculator 140 is a controller of the measurement system 100 using a glass pH sensor, and can be implemented with an embedded Central Processing Unit (CPU). The calculator 140 serves to calculate the pH value of the solution to be measured based on the output voltage of the detector 130 through 136.

Improved Response Rate

The dynamic characteristics of the measurement system 100 using a glass pH sensor in accordance with the first exemplary embodiment of the invention are expressed by Formula 3 below.

$$E_b(s) = \frac{1/(1+\beta)}{\tau s + 1} E_a(s) + \frac{\beta/(1+\beta)}{\tau s + 1} E(s) \quad \text{Formula 3}$$

$$\tau = R_1(C - \alpha C_1)/(1+\beta),$$

$$\beta = R_1 R$$

In Formula 3, $R_1$ is the resistance of the resistor 112, $C_1$ is the capacitance of the capacitor 132, R is the resistance of the equivalent internal resistor 122 of the glass pH sensor 120, C is the capacitance of the equivalent internal resistor 122 of the glass pH sensor 120, and a is the gain of the calculation amplifier 130.

As can be seen from Formula 3 above, the measurement system using the glass pH sensor can reduce the effect of the internal capacitance C of the glass pH sensor using positive feedback, performed through the feedback capacitor 132, as well as reduce the effect of the internal resistance of the glass pH sensor 120 by the resistor 112.

More specifically, the entire capacitance influencing on a time constant is $C-\alpha C_1$. If $\alpha$ is adjusted, the value can be set to approximately half of the internal capacitance of the glass pH sensor 120. As a result, there is not a problem of instability due to the positive feedback since the internal capacitance C of the glass pH sensor 120 is not sensitive.

In addition, since the resistance of the resistor 112 is smaller than the equivalent internal resistance R of the glass pH sensor 120, the influence of the time constant over a variation in the equivalent resistor 122 of the glass pH sensor 120 decreases.

In particular, if the resistor 112 provides a resistance smaller than the equivalent internal resistance R of the glass pH sensor, the time constant decreases to approximately $R_1C$, and thus the response rate is accelerated.

Calculation of Equivalent internal Resistance and Equivalent internal Voltage

In order to diagnose whether the glass pH sensor is defective or not, it is necessary to calculate the equivalent internal resistance R and the equivalent internal voltage E of the glass pH sensor 120, which, however, are difficult to calculate.

As shown in FIG. 3, the normalized output voltage Eb of the glass pH sensor 120 is $R/(R+R_1)\times Ea+R1/(R+R_1)\times E$, which depends on the equivalent internal resistance R. In particular, since the equivalent internal resistance R cannot be acquired beforehand and, especially, is time variant with respect to a change in temperature, the equivalent internal power E cannot be calculated by simply measuring the normalized output voltage Eb of the glass pH sensor 120 with respect to the constant voltage Ea.

In order to solve this problem, at least one embodiment proposes a method of simultaneously producing the equivalent internal resistance R and the equivalent internal power E of the glass pH sensor 120 by two or more attempts performed on different outer voltages Ea.

In more detail, the power supply 110 applies a square wave having a pulse width greater than the time constant to the glass pH sensor 120. Then, the calculator 140 simultaneously calculates the equivalent internal resistance R and the equivalent internal voltage E of the glass pH sensor 120 based on the output voltage of the glass pH sensor 120 with respect to two different voltages of the square wave.

Then, in order to ensure the normalized output voltage Eb of the glass pH sensor 120, a square wave is applied, the period of which is sufficient when compared to the time constant.

As such, the output voltage of the glass pH sensor 120 is a normal-state voltage, which is expressed by Formula 4 below.

$$E_{b1} = \frac{1}{1+\beta}E_{a1} + \frac{\beta}{1+\beta}E$$
$$E_{b2} = \frac{1}{1+\beta}E_{a2} + \frac{\beta}{1+\beta}E$$
Formula 4

In Formula 4 above, $Ea_1$ and $Ea_2$ indicate the voltage levels of the square wave, $Eb_1$ and $Eb_2$ indicate the output voltages of the glass pH sensor 120 in the normal-state, corresponding to the voltage levels of the square wave, and $\beta$ is $R_1/R$.

Formula 4 above, when rearranged with respect to the equivalent internal voltage E, produces Formula 5 below.

$$E = \frac{E_{a1}E_{b2} - E_{a2}E_{b1}}{(E_{a1} - E_{b1}) - (E_{a2} - E_{b2})}$$
Formula 5

In addition, Formula 4 above, when rearranged with respect to $\beta$, produces Formula 6 below.

$$\beta = \frac{R_1}{R} = \frac{(E_{a1} - E_{b1}) - (E_{a2} - E_{b2})}{E_{b1} - E_{b2}}$$
Formula 6

As such, it is possible to diagnose whether the glass pH sensor 120 is defective or not by calculating the equivalent internal resistance R of the glass pH sensor 120 based on $\beta$ as expressed above.

The pH measurement system in accordance with the first exemplary embodiment of the invention can be used as a basic solution in a variety of applications, such as chemical, biological, and environmental industries, by providing the rapid response of the glass pH sensor.

Equivalent internal Circuit of Glass pH Sensor

Figure 4:
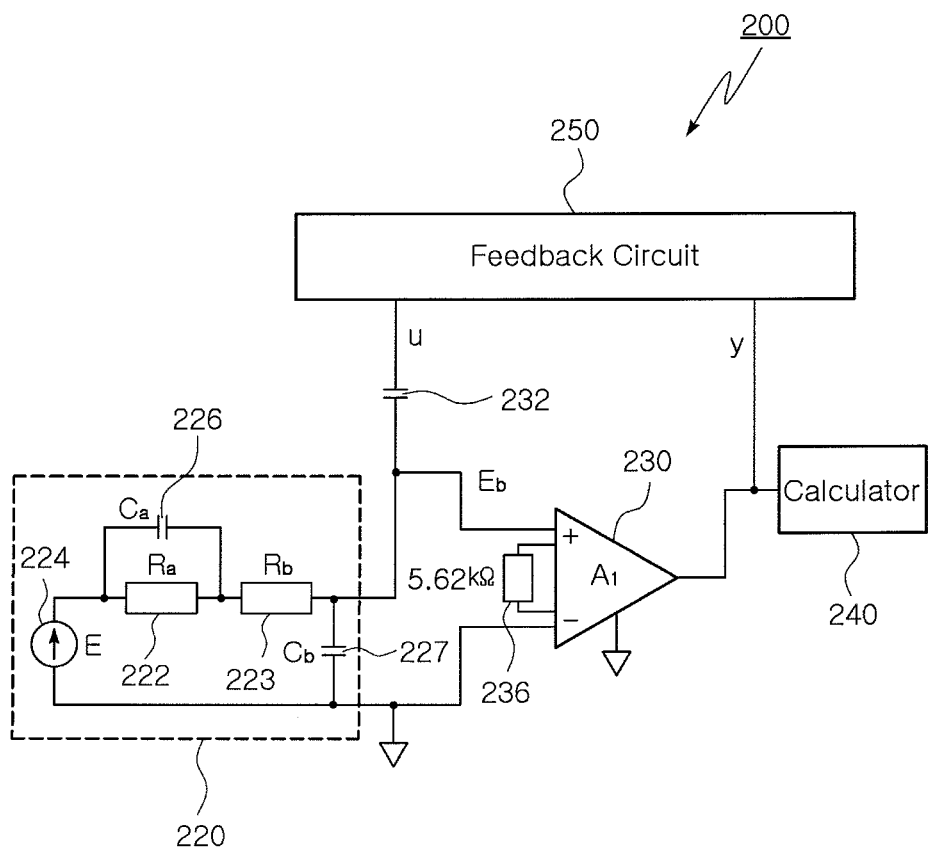
FIG. 4 is a diagram schematically illustrating a measurement system using a glass pH sensor in accordance with a second exemplary embodiment of the invention.

FIG. 4 is a diagram schematically illustrating a measurement system using a glass pH sensor in accordance with a second exemplary embodiment of the invention.

Referring to FIG. 4, the equivalent internal circuit of a glass pH sensor 220 in accordance with the second exemplary embodiment of the invention includes one equivalent power source (E) 224, two or more equivalent resistors (Ra and Rb) 222 and 223, and equivalent capacitors (Ca and Cb) 226 and 227.

The two equivalent resistors (Ra and Rb) 222 and 223 are sequentially connected in series to the equivalent power source (E) 224. The first equivalent capacitor (Ca) 226 is arranged in parallel to the first equivalent resistor (Ra) 222. The second equivalent capacitor (Cb) 227 is connected to the terminal end of the second equivalent resistor (Rb) 223, connected in series to the first equivalent resistor (Ra) 222, and is arranged in parallel to the equivalent power source (E) 224.

When a supply voltage is supplied to the glass pH sensor by the resistors, as shown in FIG. 3, degradation in Direct Current (DC) characteristics may increase pH measurement time. In contrast, when a supply voltage from the power supply is supplied to the glass pH sensor without passing through the resistor, as shown in FIG. 4, DC characteristics can be enhanced, thereby reducing pH measurement time.

Figure 5:
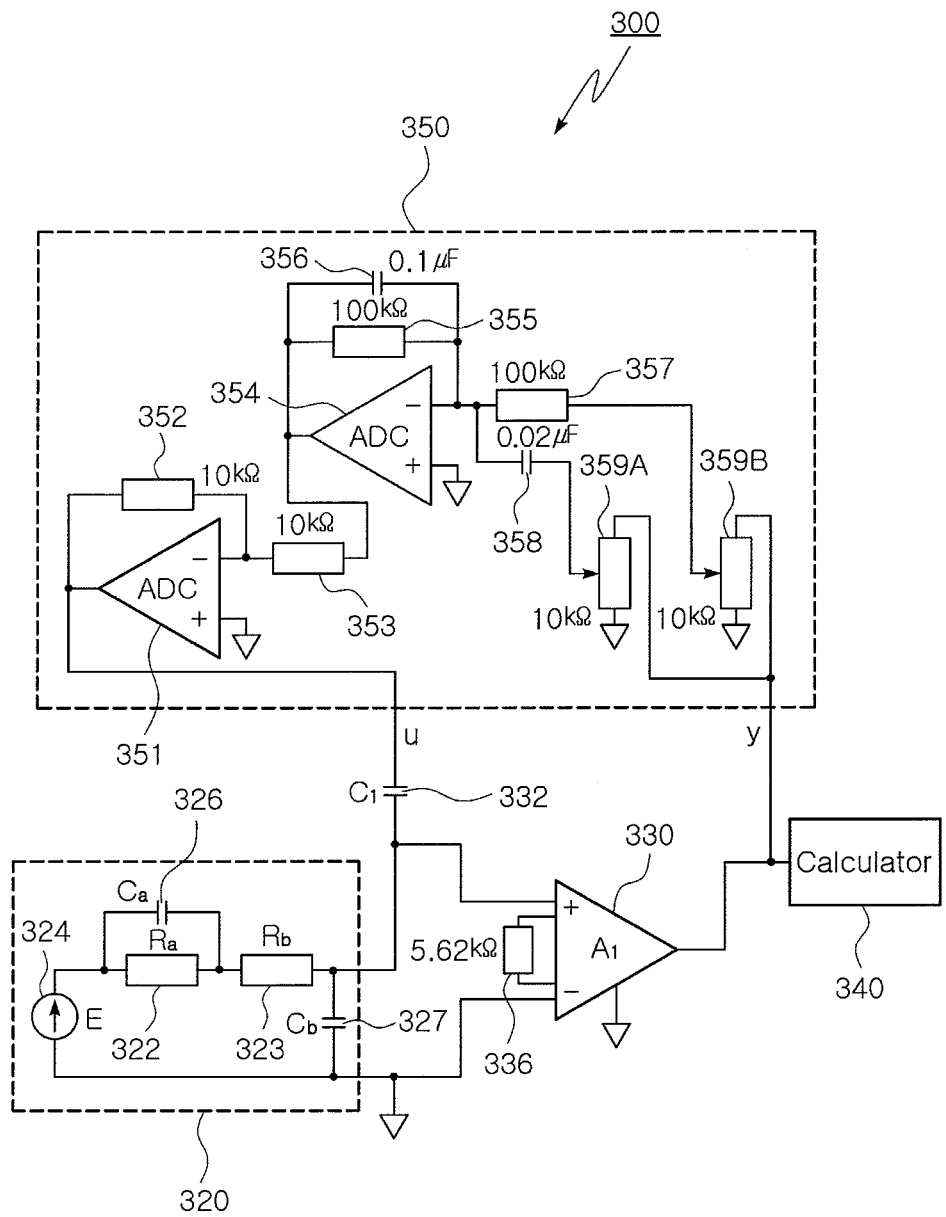
FIG. 5 is a diagram schematically illustrating a measurement system using a glass pH sensor in accordance with a third exemplary embodiment of the invention.

FIG. 5 is a diagram schematically illustrating a measurement system using a glass pH sensor in accordance with a third exemplary embodiment of the invention.

Referring to FIG. 5, a pH measurement system using a glass pH sensor in accordance with the third exemplary embodiment of the invention includes a power supply applying a supply voltage to a glass pH sensor 320, a detector 330, 332, and 336 detecting the output voltage of the glass pH sensor 320, and a calculator 340 calculating the pH of a solution based on the detected output voltage of the glass pH sensor 320. The pH measurement system also includes a feedback circuit 350 through which the output voltage of the glass pH sensor 320 is fed back to the detector 330, 332 and 336.

Feedback Circuit

The feedback circuit 350 includes two or more Analog-Digital (AD) converters 351 and 354, a plurality of resistors 352, 353, 355, 357, 359A, and 359B, and capacitors 356 and 368. The feedback circuit 350 is located between the glass pH sensor 320 and the calculator 340.

In the pH measurement system using a glass pH sensor in accordance with the third exemplary embodiment of the invention, dynamic characteristics are expressed by Formula 7 below.

$$G_{GLASS}(s) = (b_1 s + 1)/(a_2 s^2 + a_1 s + 1)$$
Formula 7

In the pH measurement system shown in FIG. 5, the transition function between the output function Y(s) and the feedback function U(s) of the detector is expressed by Formula 8 below.

$$U(s) = (k_2 s + k_1) Y(s)/\tau_F s + 1$$
Formula 8

In Formula 8, $k_2$ is a parameter that reduces $a_2$ in Formula 3 above. In addition, $k_2$ also has an effect on $a_1$ since the glass pH sensor 320 and the feedback system are interactively connected to each other by the capacitor C1 as shown in FIG. 5. Accordingly, multiple times of repetitive executions are required to select $k_1$ and $k_2$.

In the feedback circuit 350 shown in FIG. 5, the feedback and the parameters $k_1$ and $k_2$ are adjusted by available resistors 359A and 359B, and the filter time constant $\tau F$ is fixed. In this case, a calculation amplifier INA116 is used for $a_1$. In addition, when a test including an analog circuit is performed, the resistances of the variable resistors for $k_1$ and $k_2$ are adjusted prior to floating response.

In addition, the feedback circuit 350 can be implemented with an embedded CPU system.

Accordingly, the embedded CPU system can adjust a feedback voltage by calculating the production of Formula 8 above using Formula 9 below.

$$z_k = e^{-h/\tau_F} z_{k-1} + (1 - e^{-h/\tau_F}) y_k, \text{ and}$$

$$u_k = (k_2/\tau_F) y_k + (k_1 - (k_2/\tau_F)) z_k$$
Formula 9

In Formula 9, h is sampling time, and the subscript k indicates kth sampling. Formula 6 above can be processed by an embedded CPU, which is small and inexpensive. In this case, C8051F350 can be used as the embedded CPU.

Figure 6:
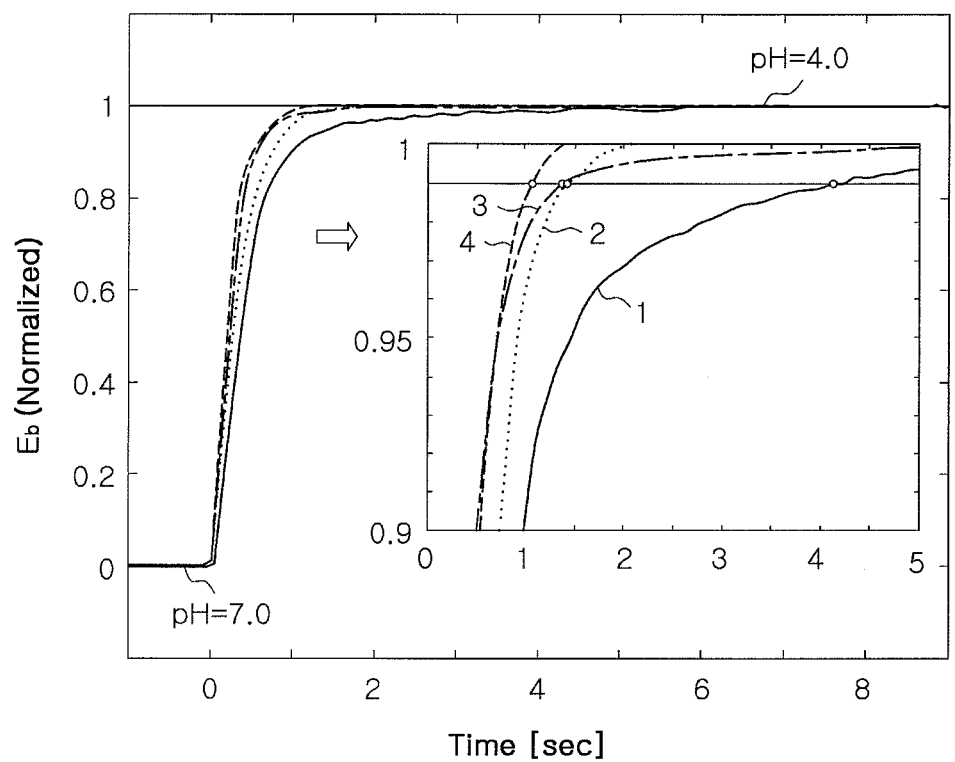
FIG. 6 is a graph illustrating the pH measurement time of a pH measurement system using a pH sensor in accordance with an exemplary embodiment of the invention.

FIG. 6 is a graph illustrating the pH measurement time of a pH measurement system using a pH sensor in accordance with an exemplary embodiment of the invention.

The graph in FIG. 6 illustrates the pH measurement times of a solution, conducted by a pH measurement system in accordance with an exemplary embodiment of the invention and a conventional pH measurement system.

As shown in FIG. 6, it can be appreciated that the pH measurement time of a solution is about 4 seconds in profile 1, in which a feedback circuit is not used.

In contrast, it can be appreciated that the pH measurement time of a solution is about 1 second in profile 4, in which a feedback voltage U(s) to be an input to the detector is adjusted using a feedback circuit.

As a result, the pH measurement time, conducted by the pH measurement system in accordance with an exemplary embodiment of the invention, is reduced to about ⅓ when compared to the pH measurement time, conducted without the proposed feedback circuit.

Diagnosis of pH Measurement System

Since the characteristics of the glass pH sensor are frequently varied, the dynamic characteristics of the pH measurement system are periodically examined and the pH measurement system is readjusted. For this purpose, a minor step change u(t) can be added.

For example, when a series of pulses (10 nA or less) is applied to the glass pH sensor, both the equivalent internal resistance and the equivalent voltage of the glass pH sensor can be measured. The internal resistance, measured in this manner, is used for the diagnosis of the glass pH sensor.

Figure 7:
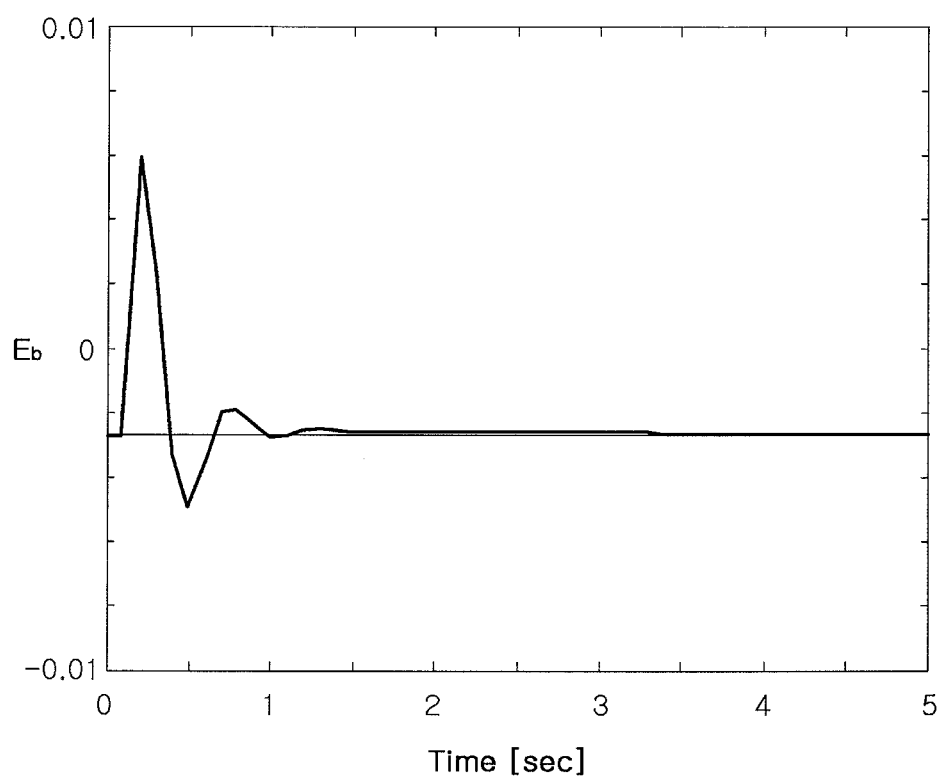
FIG. 7 is a graph illustrating the response time of a pH measurement system in accordance with an exemplary embodiment of the invention.

In particular, referring to FIG. 7, a graph represents the response time of an embedded CPU system. Specifically, the response time of the embedded CPU system is about 1 second. If a measured response time is much longer than a given response time on the basis of this value, the proposed measurement system is readjusted.

If the readjusted system fails to satisfy the given response time, the glass pH sensor can be replaced. This diagnosis process can be carried out by the embedded CPU system.

This, as a result, makes it possible to rapidly measure pH values by reducing the measurement response time of the glass pH sensor using the feedback circuit in accordance with an exemplary embodiment of the invention. In addition, since the feedback circuit is realized by the embedded CPU system, it is possible to diagnose whether the pH system is defective or not so that the follow-up measures can be properly performed.

The foregoing descriptions of specific exemplary embodiments of the pH measurement system using a glass pH sensor in accordance with the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof It is intended that the scope of the invention be defined by the Claims appended hereto and their equivalents.

What is claimed is:

1. A pH measurement system using a glass pH sensor, comprising:
  a power supply applying a voltage to the glass pH sensor through a resistor, wherein the resistor has a resistance of at least ten times less than an equivalent internal resistance of the glass pH sensor;
  a detector detecting an output voltage of the glass pH sensor; and
  a calculator calculating a pH of a solution based on the detected output voltage.

2. The pH measurement system in accordance with claim 1, wherein the detector includes a calculation amplifier and a feedback capacitor.

3. The pH measurement system in accordance with claim 2, wherein the glass pH sensor has a time constant expressed by $R_1(C-\alpha C_1)/(1+\beta)$ where $R_1$ is the resistance of the resistor, $C_1$ is the capacitance of the glass pH sensor, R is the equivalent internal resistance of the glass pH sensor, C is the equivalent internal capacitance of the glass pH sensor, $\alpha$ is the gain of the calculation amplifier, and $\beta$ is $R_1/R$.

4. The pH measurement system in accordance with claim 3, wherein the power supply provides a square wave, and wherein the calculator produces $\beta$ based on the output voltage of the glass pH sensor with respect to two different voltages of the square wave.

5. The pH measurement system in accordance with claim 4, wherein the square wave has a pulse width greater than the time constant.

6. The pH measurement system in accordance with claim 4, wherein the output voltage of the glass pH sensor is a normalized voltage.

7. The pH measurement system in accordance with claim 4, wherein the calculator produces the equivalent internal voltage of the glass pH sensor based on the output voltage of the pH glass sensor with respect to the two different voltages of the square wave.

8. The pH measurement system in accordance with claim 4, wherein the calculator produces the equivalent internal resistance of the glass pH sensor based on $\beta$ in order to enable diagnosis on whether the glass pH sensor is defective or not.

9. The pH measurement system in accordance with claim 1, wherein the glass pH sensor comprises an equivalent circuit, which includes:
  one equivalent power source;
  two or more equivalent resistors connected in series to the equivalent power source;
  a first equivalent capacitor connected in parallel to the first equivalent resistor; and
  a second equivalent capacitor connected in series to the second equivalent resistor.

10. The pH measurement system in accordance with claim 9, further comprising a feedback circuit provided between the glass pH sensor and the calculator, wherein the feedback circuit receives the output voltage of the glass pH sensor from the detector, generates a feedback voltage by adjusting the output voltage through a variable resistor, and reapplies the feedback voltage to the glass pH sensor.

11. The pH measurement system in accordance with claim 9, wherein the feedback circuit comprises an embedded central processing unit.

12. The pH measurement system in accordance with claim 9, wherein dynamic characteristics of the glass sensor are expressed by following Formula:

$$G_{GLASS}(s)=(b_1s+1)/(a_2s^2+a_1s+1),$$

where $a_1$, $a_2$, $b_1$ are constants that determine the dynamic characteristics of the glass pH sensor.

13. The pH measurement system in accordance with claim 9, wherein a transition function between the output voltage detected by the detector and the feedback voltage to be inputted again into the detector is expressed by following Formula:

$$U(s) = (k_g s + k_1) Y(s) / \tau_F s + 1,$$

where $Y(s)$ is the output voltage of the glass pH sensor, $U(s)$ is the feedback voltage, $t_F$ is the time constant of the glass pH sensor, $k_1$ and $k_2$ are variables that vary according to a variable resistance.

14. The pH measurement system in accordance with claim 11, wherein the embedded central processing unit adjusts the feedback voltage based on a result, obtained by calculating following Formulas:

$$z_k = e^{-h/\tau_F} z_{k-1} + (1 - e^{-h/\tau_F}) y_k, \text{ and}$$

$$u_k = (k_2/\tau_F) y_k + (k_1 - (k_2/\tau_F)) z_k,$$

where h is sampling time, and the subscript k indicates $k^{th}$ sampling.

* * * * *